US00PP11082P

United States Patent [19]

Berres

[11] Patent Number: Plant 11,082

[45] Date of Patent: Oct. 5, 1999

[54] OSTEOSPERMUM PLANT NAMED 'MIRA'

[75] Inventor: Marcus Berres, Bingen-Bedesheim, Germany

[73] Assignee: InnovaPlant GmbH & Co. KG, Gensingen, Germany

[21] Appl. No.: 09/004,810

[22] Filed: Jan. 9, 1998

[51] Int. Cl.[6] ..... A01H 5/00

[52] U.S. Cl. ..... Plt./360

[58] Field of Search ..... Plt./360

[56] References Cited

U.S. PATENT DOCUMENTS

| | | | |
|---|---|---|---|
| P.P. 10,337 | 4/1998 | Sorensen | Plt./360 |
| P.P. 10,339 | 4/1998 | Larsen | Plt./360 |
| P.P. 10,353 | 4/1998 | Larsen | Plt./360 |
| P.P. 10,595 | 9/1998 | Kanno | Plt./360 |
| P.P. 10,603 | 9/1998 | Kanno | Plt./360 |

*Primary Examiner*—Howard J. Locker
*Assistant Examiner*—Kent L. Bell
*Attorney, Agent, or Firm*—C. A. Whealy

[57] ABSTRACT

A distinct cultivar of Osteospermum plant named 'Mira', characterized by its compact, upright and outwardly spreading growth habit; dense foliage; erect flower stems; moderate to vigorous growth rate; intense purple ray florets with darker purple stripes; dark violet blue disc florets; numerous inflorescences per plant; continuous flowering; and good garden performance.

1 Drawing Sheet

The present invention relates to a new and distinct cultivar of Osteospermum plant, botanically known as *Osteospermum eklonis* and referred to by the cultivar name 'Mira'.

The new cultivar is a product of a planned breeding program conducted by the inventor in Gensingen, Germany. The objective of the breeding program was to create new compact Osteospermum cultivars with early and continuous flowering.

The new cultivar originated from a cross made by the inventor of the commercial *Osteospermum ecklonis* cultivar 'Sunny Lady' (disclosed in U.S. Plant Pat. No. 10,353) as the female, or seed, parent and the inventor's proprietary selection of *Osteospermum ecklonis,* code No. 5255 as the male, or pollen, parent, The new Osteospermum was selected by the inventor from the progeny of this cross in a controlled environment in Gensingen, Germany, during the summer of 1993.

In side-by-side comparisons in Gensingen, Germany, under commercial practice, plants of the new Osteospermum are different from plants of the female parent, the cultivar 'Sunny Lady', in the following characteristics:

1. Leaves of plants of the new Osteospermum are smaller and more rounded than leaves of plants of the cultivar 'Sunny Lady'.
2. Plants of the new Osteospermum flower earlier than plants of the cultivar 'Sunny Lady'.
3. Ray florets of plants of the new Osteospermum exhibit more noticeable longitudinal striping than plants of the cultivar 'Sunny Lady'.

Plants of the new Osteospermum differ from plants of the male parent, the proprietary selection code No. 5255, in ray floret color and leaf shape.

Asexual reproduction of the new cultivar by terminal cuttings taken at Gensingen, Germany, has shown that the unique features of this new Osteospermum are stable and reproduced true to type in successive generations.

The following traits have been repeatedly observbed and are determined to be the unique characteristics of 'Mira'. These characteristics in combination distinguish 'Mira' as new and distinct cultivar:

1. Compact, upright and outwardly spreading growth habit with dense foliage and erect flower stems.
2. Moderate to vigorous growth rate.
3. Intense purple ray florets with darker purple stripes and dark violet blue disc florets.

4. Numerous infloresces per plant. Plants flower continuously.
5. Good garden performance.

The cultivar 'Mira' has not been observed under all possible environmental conditions. The phenotype may vary somewhat with variations in environment such as temperature, daylength and light intensity, without, however, any variance in genotype.

BRIEF DESCRIPTION OF THE PHOTOGRAPHS

The accompanying colored photographs illustrate the overall appearance of the new cultivar, showing the colors as true as it is erasonably possible to obtain in colored reproductions of this type.

The photograph at the top of the sheet comprises a top perspective view of a typical flowering plant of 'Mira'.

The photograph at the bottom of the sheet is a close-up view of a typical inflorescence of 'Mira'. Foliage and floret colors in the photographs may appear different from the actual colors due to light reflectance.

DETAILED BOTANICAL DESCRIPTION

In the following description, color references are made to The Royal Horticultural Society Colour Chart except where general terms of ordinary dictionary significance are used. The following observations and measurements describe plants grown outdoors in containers during the spring and summer in Encinitas, Calif. Measurements and numerical values represent averages for typical flowering plants.

Botanical Classification: *Osteospermum ecklonis* cultivar 'Mira'.

Parentage:

*Female, or seed, parent.*—*Osteospermum ecklonis* cultivar 'Sunny Lady' (disclosed in U.S. Plant Pat. No. 10,353).

*Male, or pollen, parent.*—Proprietary selection of *Osteospermum ecklonis,* code No. 5255.

Propagation:

*Type.*—By terminal cuttings and by tissue culture.

*Time to initiate roots.*—Summer: About 15 days at 22° C. Winter: About 21 days at 22° C.

*Time to develop roots* (*time required to produce a rooted cutting*).—Summer: About 21 days at 22° C. Winter: About 25 days at 22° C.

*Rooting habit.*—Thick, fibrous and somewhat branched.

Plant description:

*Appearance.*—Perennial herbaceous container and garden plant. Upright and outwardly spreading growth habit. Dense foliage and erect flower stems. Freely branching and growth rate is moderate to vigorous.

*Plant height.*—About 35 cm.

*Plant spread.*—About 80 cm.

*Stem description.*—Diameter: About 4 mm. Strength: Strong, flexible. Color: Upper surface: 183B. Lower surface: 144B.

*Foliage description.*—Leaves alternate, single. Length, fully expanded leaves: About 7 cm. Width, fully expanded leaves: About 2.5 cm. Shape: Oblanceolate/spatulate. Apex: Acuminate. Base: Attenuate, sessile. Margin: Young leaves, mostly entire; mature leaves, widely-spaced teeth, ciliate. Aspect: Flat to recurved. Texture: Leathery with very fine pubescence on both surfaces, sticky. Fragrance: Strongly fragrant, typical of species. Color: Young foliage, upper surface: 147A. Young foliage, under surface: 147B. Fully expanded foliage, upper surface: 147A. Fully expanded foliage, under surface: 147B. Attenuated leaf base: 144A/147B. Venation, upper surface: 144A/147B. Venation, under surface: 147C.

Inflorescence description:

*Appearance.*—Daisy-type composite inflorescence from. Inflorescences borne on terminals above foliage, arising from leaf axils. Disc and ray florets arranged acropetally on a capitulum. One inflorescence per flowering stem. Inflorescences are long-lasting on the plant lasting about 10 to 14 days. Inflorescences persistent.

*Flowering response.*—Plants flower continuously from April to October in the Northern Hemisphere.

*Fragrance.*—Slight, typical of species.

*Inflorescence size.*—Diameter: About 6 cm. Depth (height): About 1.5 cm. Diameter of disc: About 1 cm.

*Opening inflorescences.*—Length: About 1.5 cm. Width: About 1 cm. Shape: Pointed, ovoid. Color: 144A.

*Ray florets.*—Length: About 3 cm. Width: About 8 mm. Shape: Oblanceolate/oblong. Apex: Tri-dentate. Margin: Entire. Texture: Velvety, smooth. Number of ray florets per inflorescence: About 20. Color: When opening: 78A. Mature, upper surface: 80B with darker, 80A, longitudinal stripes. Floret color may fade to lighter purple with subsequent development. Mature, under surface: 79D with darker, 79A, longitudinal stripes.

*Disc florets.*—Length: About 7.5 mm. Width: About 1 mm at base, flaring to about 2 mm at apex. Shape: Tubular, funnel-shaped, fluted at apex. Number of disc florets per inflorescence: Numerous. Color: Darker than 93A.

*Peduncle.*—Length: About 10 cm. Diameter: About 2 mm. Aspect: Strong and wiry, inflorescences held erect above foliage. Texture: Very fine pubescence. Color: 144A to purple at distal end.

*Sepals.*—Appressed to ray florets. Shape: Narrowly linear with pointed apex. Quantity: About 16 per inflorescence. Texture: Very fine short hairs. Color: 144A.

*Reproductive organs.*—Adroecium: Present on disc florets only. Anthers: One per disc floret, 5-parted. Pollen: Golden yellow, moderate. Gynoecium: Present on ray disc florets. Stigma: Bipartite. Style: Purple. Ovary: Inferior, green in color.

Disease resistance: No known Osteospermum diseases observed to date on plants grown under commercial production.

Seed production: Seed production has not been observed.

It is claimed:

1. A new and distinct cultivar of Osteospermum plant named 'Mira', as illustrated and described.

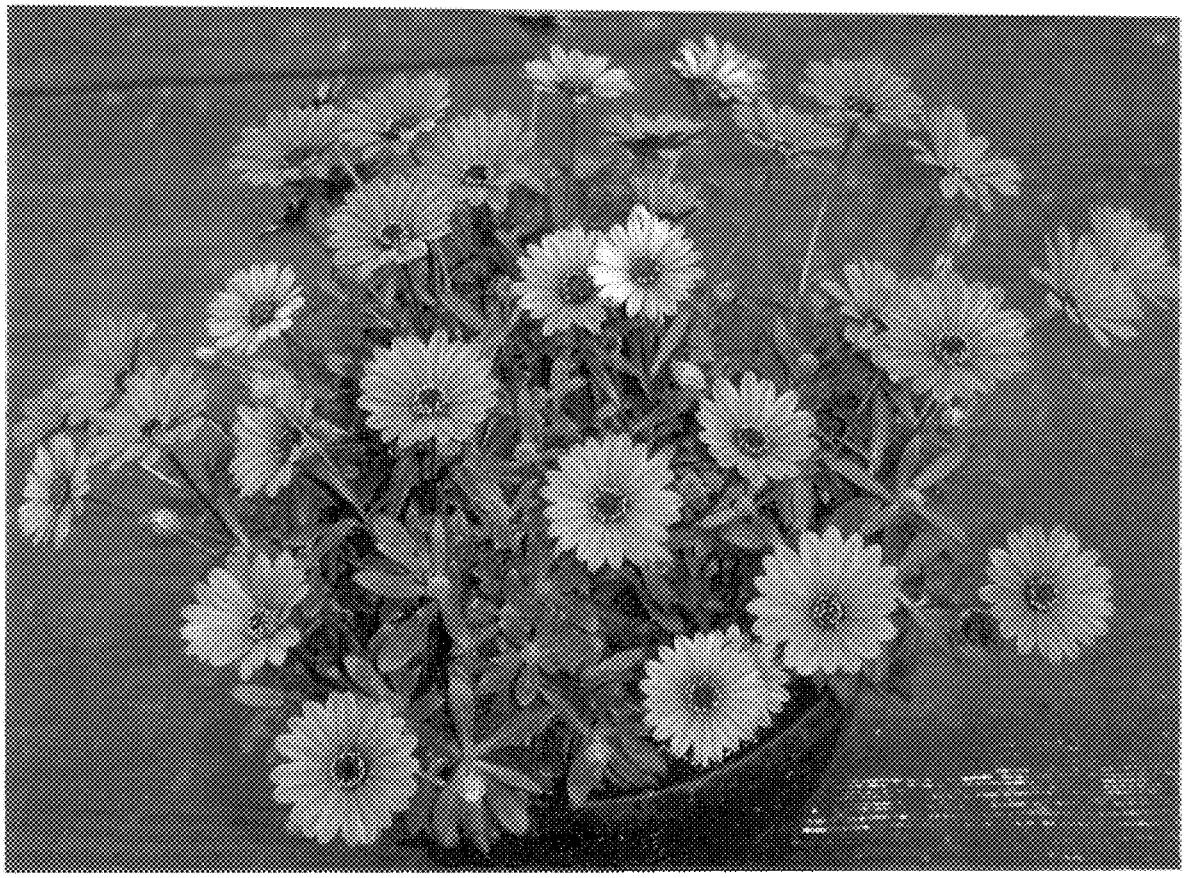
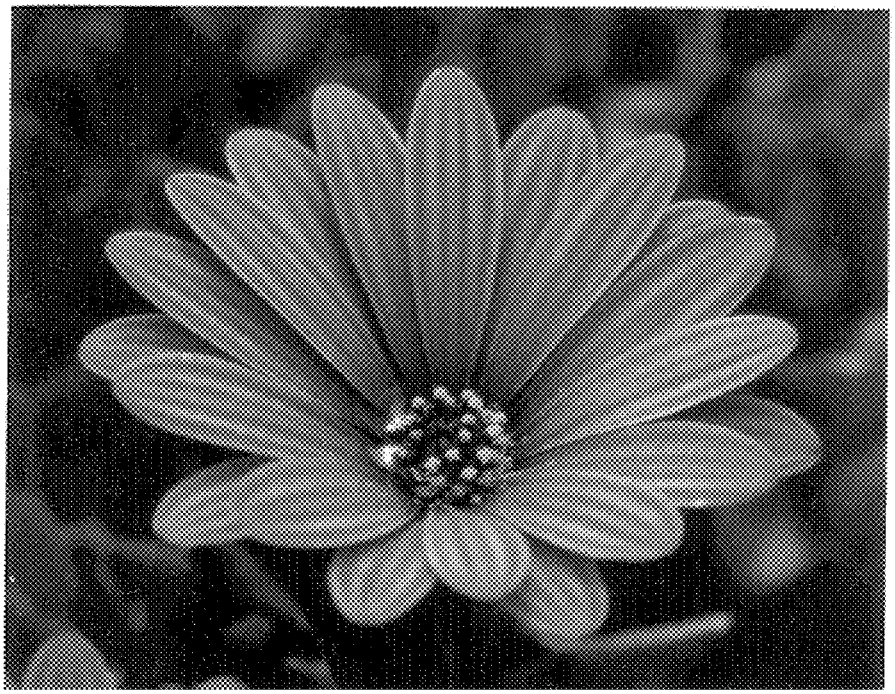

* * * * *